United States Patent [19]

Sakai et al.

[11] 4,032,403

[45] June 28, 1977

[54] PROCESS FOR THE PRODUCTION OF SACCHARIFIED STARCH PRODUCTS WHEREIN MALTOSE IS THE PREDOMINANT CONSTITUENT

[75] Inventors: Shuzo Sakai; Naoto Tsuyama, both of Okayama, Japan

[73] Assignee: Kabushiki-Kaisha Hayashibara Seibutsukagaku Kenkyujo, Okayama, Japan

[22] Filed: July 10, 1975

[21] Appl. No.: 594,680

[30] Foreign Application Priority Data

July 17, 1974 Japan ............................. 49-81949
Nov. 7, 1974 Japan ............................ 49-128638

[52] U.S. Cl. ............................... 195/31 R; 195/11
[51] Int. Cl.² ........................................ C12D 13/02
[58] Field of Search ............. 195/11, 7, 31 R, 66 R, 195/62, 65, 13

[56] References Cited

UNITED STATES PATENTS 3,677,896  7/1972  Kurimoto et al. ............... 195/31 R
3,795,584  3/1974  Mitsuhashi et al. ............. 195/31 R

OTHER PUBLICATIONS

Robyt et al., "Isolation, Purification and Characterization of a Maltotetrose-Producing Amylase from Pseudomonms Stutzei", Arch Biochem. Biophysics, vol. 145 (1971) pp. 105-114.
Parrish et al., "Actions of Starch Carbohydrases on Chemically Modified Maltodextrins", Arch Biochem Biophysics, vol. 137 (1970) pp. 185-189.
Bird et al., "The Action of Some 2-Amylases on Amylose", Biochemical Journal, vol. 56, pp. 86-99 (1954).
Whistler et al., Starch : Chemistry and Technology, vol. 1, Academic Press, New York and London (1965) pp. 160-163.
Greenwood et al., "The 2-Amylolysis of Starch", Die Starke, vol. 17, No. 7, pp. 219-225 (1965).
Feniksova et al., "Products of Starch Hydrolysis by 2-Amylase of Aspergillus Oryzae 3-9-15", Chemical Abstracts, vol. 74, No. 19, p. 45, Abs. No. 94697k (1971).

*Primary Examiner*—Raymond N. Jones
*Assistant Examiner*—Thomas G. Wiseman
*Attorney, Agent, or Firm*—Browdy and Neimark

[57] ABSTRACT

A process for the production of saccharified starch products in which maltose is the predominant constituent characterized by subjecting a starch hydrolysate simultaneously or successively to the action of an enzyme(s) with a maltotriose-decomposing activity versus maltose-decomposing activity ratio of 2.5 or higher and which is obtained from higher plant and/or bacterial source and to the action(s) of a maltogenic enzyme(s), purifying, concentrating and recovering the resulting saccharified starch products.

4 Claims, No Drawings

PROCESS FOR THE PRODUCTION OF SACCHARIFIED STARCH PRODUCTS WHEREIN MALTOSE IS THE PREDOMINANT CONSTITUENT

FIELD OF THE INVENTION

The present invention relates to a process for the production of saccharified starch products wherein maltose is the predominant constituent, characterized in that the maltotriose content of the products is reduced while the maltose purity is improved by subjecting a starch hydrolysate simultaneously or successively to the action(s) of an enzyme(s), possessing a maltotriose-decomposing activity versus maltosedecomposing activity ratio of 2.5 or higher and which is derived from higher plant and/or from a bacterial culture, and the action(s) of maltogenic enzyme(s) during the production of saccharified starch products wherein maltose is the predominant constituent. Hereinafter throughout the present specification enzymes with a maltotriose-decomposing activity and a maltosedecomposing activity will be designated, respectively, maltotriase and maltase.

BACKGROUND OF THE INVENTION

Recently, many advantageous features have been found in maltose and such recognition has led to the realization of an expansion of its uses. Thus, saccharified starch products wherein maltose is the predominant constituent are receiving great demands.

Conventionally, starch hydrolysates with a maltose purity in the range of 40–50%, w/w (all percents and parts will be given hereinafter by weight, dry solid basis or d.s.b. unless specified otherwise) have been obtained, by subjecting liquified starch to the action of malt amylase (a maltogenic enzyme). More recently, saccharified starch hydrolysates with a maltose purity more than 50% have become obtainable with relative ease by a combination of starch-debranching enzyme and beta-amylase.

In starch hydrolysates with a predominant maltose content prepared with conventionally-known maltogenic enzyme(s), for example alpha-amylase, beta-amylase and starch-debranching enzyme, however, maltotriose is formed necessarily. Further, since the maltotriose is substantially outsusceptible to such maltogenic enzyme(s), there was a limit to the increment of maltose purity. Investigations of the present inventors have shown that a conversion of the maltotriose, formed abundantly in the saccharified starch hydrolysates, into maltose is necessary to attain further maltose purity improvement.

SUMMARY OF THE INVENTION

In order to obtain saccharified starch products with higher maltose purity by the decomposition of the maltotriose present in the products, the present inventors drew their attention towards the higher plant and bacterial maltotriase which so far received practically no attention, and discovered that the employment of an enzyme(s) with a maltotriase versus maltase ratio (hereinafter referred to as specified activity ratio) of 2.5 or higher is effective in maltose purity improvement. Based on the discovery the inventors performed extensive screening of higher plants and bacteria and screened-out those possessing enzyme(s) with said specified activity ratio.

The screening resulted in the findings that such enzyme(s) is present in higher plants, for example tubers, roots, tops, leaves, stems, seeds, grains and germinated grains, and also that bacteria of genera *Pseudomonas, Xanthomonas, Flavobacterium, Escherichia, Klebsiella, Enterobacter, Erwinia, Micrococcus, Sarcina, Lactobacillus, Arthrobacter, Bacillus, Aeromonas, Cytophaga,* and *Streptomyces* produce enzymes with said specified activity ratio.

The inventors have established that the final saccharified starch products according to the present invention obtained by dual saccharifications, more particularly, allowing enzyme(s) or mixture thereof with said specified activity ratio to act during or after the initial saccharification, i.e. saccharification with maltogenic enzyme(s) according to prior art, will possess considerably higher maltose purity in comparison with conventional saccharified starch hydrolysates.

DESCRIPTION OF THE PREFERRED EMBODIMENTS

Any starch is employable in the practice of the present invention regardless of origin, i.e., cereal, tuber or root starches, and amylose/amylopectin proportion. Firstly, a starch suspension is gelatinized or liquefied. The liquefaction is carried out with acid and/or enzyme to a D.E. (dextrose equivalent), preferably, to not more than 25. Thereafter the liquefied starch is saccharified by subjecting the starch to the action of known maltogenic enzyme(s), e.g. beta-amylase or beta-amylase and starch-debranching enzyme. In general, enzymes derived and prepared from wheat bran (cf. Specification of Japanese Patent Publication 70-18937), soybean and sweet potato are used as beta-amylase. For starch-debranching enzyme, microbial enzymes, such as those derived from any culture broth of genera *Escherichia intermedia* ATCC 21073, *Aerobacter aerogenes* ATCC 8724, *Pseudomonas amyloderamosa* ATCC 21262, *Corynebacter sepedonicum* IFO 3306, *Aeromonas hydrophyla* IFO 3820, *Flavobacterium esteroacromaticum* IFO 3751, *Vibro metschnikovii* IFO 1039, *Actinoplanes philippinesis* ATCC 12427 and *Streptosporangium roseum* ATCC 12428 as described in Japanese Patent Publications 68-28939, 69-8070, 70-9229, 70-16788, 71-28151, and 73-18826 are employable.

Depending on the method used for the process of production, the resultant saccharified starch hydrolysate will have a maltotriose content, in general, of about 5 to about 25% and its maltose purity limit would be about 50–93%. By allowing an enzyme(s) derived from higher plants and/or culture of bacteria and which have said specified activity ratio during saccharification along with conventionally-known maltogenic enzyme(s), or allowing the former enzyme to saccharify on the saccharified starch hydrolysates upon completion of saccharification with such known maltogenic enzymes(s), the maltotriose content, present in the initial saccharified starch hydrolysate and which prevents further improvement in maltose purity, is majorly decomposed and the maltose purity of the final saccharified starch product can be improved by an additional approximate 3–15%.

Then term "maltogenic enzyme(s)" as used in the present invention means an enzyme capable of producing maltose without substantial decrease in maltose purity. The saccharifed starch products prepared in accordance with the present invention were heated to inactivate the enzymatic activity therein, filtered, decolorized with activated carbon, deionized with ion exchange resins, and prepared into syrup, crystalline or powder forms by concentration, crystallization or spray drying. The yield was 96-99% based on material, d.s.b.

A typical example of saccharification conditions will be described. The maltose purity of a saccharified starch hydrolysate, prepared by either saccharifying a 20-40% aqueous acid- or enzyme-liquefied starch hydrolysate with a D.E. of 5-20, or saccharifying a starch hydrolysate with a D.E. not more than 5 at a temperature of about 60° C using malt amylase, will be at the highest 50-60%, thus the production of starch hydrolysates with higher maltose purity has so far been rendered extremely difficult.

By adding an enzyme(s) with the specified activity ratio of 2.5 or higher which is derived from higher plants and/or obtained by culture of bacteria in an amount of 0.05 units or more per gram saccharified starch hydrolysates, d.s.b., to the above saccharified starch hydrolysates during or after its saccharification process and incubating the mixture at a temperature from 30° to 55° C and pH 4.0-8.0 an attainment of a maltose purity of about 60-75% in the resultant saccharified starch products was easily possible.

Specifically, in the saccharified starch products prepared in accordance with the invention, an approximately 1.3 to 1.6 fold increment in fermentable sugars was attainable along with the raise in maltose purity.

Further, a saccharified starch hydrolysate containing about 90-93% maltose is obtained by saccharifying a 5-20% aqueous acid or alpha-amylase liquefied starch hydrolysates with a D.E. not more than 5 with the employment of a combination of beta-amylase and starch-debranching enzyme. In this case the improvement of the maltose purity higher than this level was generally extremely difficult. The inventors found that by further subjecting such saccharified starch hydrolysates during or after the saccharification process to the enzyme(s) possessing the specified activity ratio of 2.5 or higher similarly as above, the maltose purity can be increased to about 93 to 97% with ease, which led to the discovery of a novel process for obtaining saccharified starch products in which maltose is the predominant constituent.

Especially, the inventors found that the shape, size and appearance of the crystals obtained by purifying the saccharified starch products which possesses a maltose purity of not less than 93%, concentrating and crystallizing the resultant are extremely desirable, the eventual period required for centrifugation to recover the crystals from mother liquor (hereinafter referred to as centrifugation period), could be reduced to about ½-⅓ in comparison with conventional maltose-predominant starch hydrolysates, and that the yield of crystalline maltose can be elevated about 1.5-2.5 fold. The maltose product thus prepared is specifically suited for intravenous injection.

As described above, the inventors have discovered that with the employment of an enzyme(s) or, thereof derived from higher plants source or obtained by culture of bacteria and which has the specified activity ratio of 2.5 or higher leads to the facile accomplishment of the improvement of maltose purity, which was so far extremely difficult with the employment of the conventionally-used maltogenic enzyme(s), and invented a novel process for the production of maltose-predominant saccharified starch products.

The methods for enzymatic activity assay and quantitative determination of sugar composition were carried out and calculated as follows. *Maltotriase activity assay:* Ten ml of a 0.1M acetate buffer solution, pH 6.0, containing 0.55%, w/v, maltotriose was reacted with 0.5ml of a given enzyme solution at 40° C, then the glucose formed per ml of reaction mixture was assayed according to the glucose-oxidase method described in Anal. Biochem., Vol. 30, p.467, J. B. Lloyd and W. J. Whelan, (1969) and the amount of enzyme which effected hydrolysis of one $\mu$ mole of maltotriose per minute at 40° C was designated as one unit of maltotriase. *Maltase activity assay:* Quantitative assay and calculation were carried out similarly as maltotriase activity except that maltotriose was replaced with maltose. *Starch-decomposing activity assay:* Quantitative assay and calculation were carried out similarly as maltotriase activity except that soluble starch was used in place of maltotriose. *Quantitative determination of sugar composition:* Developed paper chromatograms obtained in accordance to the method described in "Sugar Handbook", p.686-687, editors, Hamaguchi and Sakurai; publisher, Asakura Shoten Inc., Tokyo, Japan (1964) were fractionated into each composition which was quantitatively determined by the anthrone method and expressed in percentage.

The method for the preparation of enzymes with the specified activity ratio from higher plants will be now described.

The inventors have discovered that the enzymes with the said specified activity ratio which are employable in the invention and mixtures thereof are widely present in higher plants, for example in their tubers, roots, leaves, stems, grains and germinated grains or seeds. More particularly, the sources include tubers, roots and subterranean stems of potato, carrot, radish and sweet potato, leaves and stems of cabbage and spinach, grains and germinated grains of hulled rice, rice bran, barley, barley malt, wheat, wheat bran, wheat germ, grain sorghum, sawa millet, canary seed, soybean, defatted soybean, germinated soybean, mung bean, alfalfa, corn maize and corn germ. The enzymes are separated from the plants according to methods commonly used. For example, extraction, rasping and pressing are distinguishably suited. Further, one or more means of treatment such as those with ultrasonics, freezing and thawing, autolysis and cell-wall-decomposing enzyme may be used if necessary.

Generally, for juicy specimens, for example leaves, stems, roots and tubers, rasping and pressing are preferable, while for relatively low-moisture specimens, for example dry seeds and grains, the spraying or dipping extraction method wherein an appropriate amount of solvent, for example more than an equivalent weight based on the specimen of water, buffer solution, salt solution or urea solution, is used is preferable. The suspension thus obtained which contains the enzyme(s) is subjected to filtration or centrifugation to separate it into residue and filtrate or supernatant. In case the specified activity ratio of the thus obtained enzyme(s) is lower than 2.5, or either an enzyme with a higher activity ratio is desired the enzyme product is subjected to purification such as fractionation to elevate the ratio. If the activity is excessively low, preferably, the product is concentrated by either precipitation with ammonium sulfate or organic solvent, or concentrated in vacuo.

The preparation of bacterial enzyme with the specified activity ratio of 2.5 or higher will be described.

The cultivation of various bacteria are usually carried out at 20°–35° C under a stationary or aeration-agitation conditions for one to five days on a liquid culture medium containing carbon, nitrogen and inorganic sources and traces of growth factors, sterilized at a temperature of 120° C for 10–30 minutes and inoculated with a bacterium..

The culture broth may be used intact as enzyme solution, or if necessary its supernatant obtained by removal of cells with filtration or centrifugation.

Alternatively, the objective endocellular enzyme may be used after treatment with ultrasonics, freezing and thawing, autolysis, cell-wall decomposing enzyme or a surface active agent, if desirable. The suspension containing the enzyme(s) derived from bacterial cells may be then separated into cell body residues and supernatant by filtration or centrifugation.

In case the specified activity ratio of the culture broth or supernatant obtained in accordance with the above-described procedures is lower than 2.5 or a higher ratio is desirable, the ratio may be increased by purification of the enzyme, for example by fractionation. In case the enzymatic activity is excessively low, the enzyme is concentrated by precipitation with ammonium sulfate or organic solvent, or by concentration in vacuo.

The partially-purified enzyme, prepared from higher plant or bacterial source in accordance with the invention and which possesses the specified activity ratio of 100 or higher, has generally an optimal pH range from about 5.0 to 7.0, an optimal temperature range from about 45° to 55° C, a stable pH range of about 4.5 to 10.0 and a stable temperature range of not higher than about 55° C, an maltotriase activity several times higher than starch-decomposing activity, but hardly any dextrinogenic activity.

The invention will be illustrated in detail with reference to some embodiments.

EXPERIMENT 1

Mixtures consisting of one part of a rasped product of roots, leaves, stems, seeds or grain, germinated seeds or grain of a variety of higher plant and five parts of water, 35° C, were allowed to stand with occasional stirring for three hours and then centrifuged. The resultant supernatants were then determined on the specified activity ratio, and maltotriase activity per gram specimen. Results were as given in Table I.

Table I

| Enzyme source | Specified activity ratio | Maltotriase, u/g |
|---|---|---|
| Soybean | 1.98 | 1.81 |
| Corn germ | 2.86 | 1.06 |
| Wheat germ | 3.10 | 6.95 |
| Wheat bran | 3.16 | 1.77 |
| Cabbage | 3.20 | 0.10 |
| Hulled rice | 3.88 | 6.51 |
| Canary seed | 6.24 | 1.43 |
| Potato | 8.17 | 0.38 |
| Malt | 9.94 | 1.57 |
| Rice bran | 11.60 | 5.39 |

EXPERIMENT 2

The soybean extracted supernatant obtained in Experiment I was brought to 0.95 saturation degree with ammonium sulfate at 4° C and then centrifuged. The precipitation portion was dissolved in 1/20M borate buffer, pH 9.0, and the resultant solution was adjusted to pH 9.0 with a trace addition of sodium hydroxide.

The solution was allowed to stand at 35° C and determined on the residual specified activity and maltotriase activity with specimens collected at 0,1,2, and 4 hours. In Table II are listed the results.

Table II

| Treatment, hr | Residual maltotriase, % | Specified activity ratio |
|---|---|---|
| 0 | 100 | 1.98 |
| 1 | 100 | 2.80 |
| 2 | 98 | 3.65 |
| 4 | 98 | 7.11 |

Aliquots of the thus obtained enzyme solutions were added individually to portions of a 20% aqueous solution of an enzymatic-starch hydrolysate with a composition of 3.7% glucose, 53.5% maltose, 20.5% maltotriose and 22.3% dextrins, in an amount of one unit per gram starch hydrolysate, d.s.b., and then the mixtures were allowed reaction at 50° C for 16 hours following a pH adjustment to pH 6.0. The results were as listed in Table III.

Table III

| Specified activity ratio | Sugar composition, % | | | |
|---|---|---|---|---|
| | $G_1$ | $G_2$ | $G_3$ | Dext |
| Non added | 3.7 | 53.5 | 20.5 | 22.3 |
| 1.98 | 24.4 | 55.6 | 3.5 | 16.5 |
| 2.80 | 16.5 | 62.9 | 3.2 | 17.4 |
| 3.65 | 13.9 | 66.2 | 3.3 | 16.6 |
| 7.11 | 11.0 | 68.7 | 3.2 | 17.1 |

Notes:
In the Table and throughout the specification, $G_1$, $G_2$ and $G_3$ represent, respectively, glucose, maltose, and maltotriose. Dext represents maltotetraose and higher molecular dextrins.

As apparent from the results, maltotriose underwent decomposition regardless of the specified activity ratio. No great variation in maltose purity of the saccharified starch products is noticable when the activity ratio is 1.98. However, the maltose purity is improved substantially as the ratio exceeds this value.

EXPERIMENT 3

Culture media of the following compositions and prepared with tap water were adjusted to pH 7.0 with either 1N-HCl or 1N-NaOH, and then sterilized by subjection to a temperature of 120° C for 20 minutes.

| Culture Medium (1), w/v% | | Culture Medium (2), w/v% | |
|---|---|---|---|
| Soluble starch | 2.0 | Pullulan | 1.0 |
| Peptone | 1.0 | Sodium acetate | 1.0 |
| Yeast extract | 0.5 | Peptone | 1.0 |
| $K_2HPO_4$ | 0.1 | Yeast extract | 0.2 |
| KCl | 0.05 | $MgSO_4 \cdot 7H_2O$ | 0.02 |
| $MgSO_4 \cdot 7H_2O$ | 0.001 | $MnSO_4 \cdot 4H_2O$ | 0.0002 |
| | | KCl | 0.01 |

| Culture Medium (3), w/v% | |
|---|---|
| Soluble starch | 2.0 |
| Soybean extracts | 5.0 |
| Yeast extract | 0.1 |

To each culture medium was inoculated one variety of bacterium strain and then the mixtures were subjected to stationary or aerobic cultivation at a temperature of 27° C or 30° C for 5 days, and the culture broths were determined on enzymatic activities. Representative results obtained with numerous test bacterial strains are listed in Table IV.

EXPERIMENT 4

Strain of *Bacillus megaterium* FERM-P 937 was cultivated according to the method described in Experiment 3. The maltotriase activity in the culture broth was 0.62u/ml and the specified activity was 1.3. The supernatant fraction of the culture broth was salted-out with ammonium sulfate and a precipitate with a saturation degree in the range of 0.2-0.9 was obtained. The activity ratio of the precipitate was identical to that of the culture broth. The activity ratio increased to 2.7, 9.6 and 21.3 after allowing aliquots of the precipitate which was dissolved in a buffer with a pH of 9.0 to stand at 35° C for respective periods of 0.5, 2.0 and 5.0 hours.

Table IV

| Microorganism | | | Medium | Cultivation conditions | | Specified activity ratio | Maltotriase (u/ml) |
|---|---|---|---|---|---|---|---|
| *Pseudomonas amyloderamosa* | ATCC | 21262 | (1) | 27° C | Aerobic | 17.7 | 1.24 |
| *Pseudomonas iodinum* | IFO | 3558 | (1) | 27° C | " | 6.7 | 0.40 |
| *Xantomonas citri* | IFO | 12213 | (1) | 30° C | " | > 100 | 2.20 |
| *Flavobacterium suaveolens* | IFO | 3752 | (1) | 30° C | " | 1.5 | 0.24 |
| *Escherichia coli* | IFO | 3044 | (1) | 30° C | " | 13.7 | 1.37 |
| *Klebsiella neumoniae* | ATCC | 8724 | (1) | 30° C | " | 5.9 | 1.07 |
| *Enterobacter aerogenes* | ATCC | 9621 | (1) | 30° C | " | 11.1 | 0.89 |
| *Erwinia aroideae* | IFO | 3830 | (1) | 30° C | " | > 100 | 1.53 |
| *Sarcina variabilis* | IFO | 3067 | (1) | 30° C | " | 17.0 | 0.27 |
| *Lactobacillus plantarum* | ATCC | 8008 | (2) | 30° C | Stationary | 5.5 | 0.72 |
| *Arthrobacter simplex* | IAM | 1660 | (1) | 30° C | Aerobic | 6.1 | 0.43 |
| *Bacillus cereus* | IFO | 3001 | (3) | 30° C | " | 5.2 | 0.94 |
| *Bacillus firmus* | IFO | 3330 | (3) | 30° C | " | 1.3 | 0.25 |
| *Bacillus megaterium* | FERM- | P937 | (3) | 30° C | " | 1.3 | 0.62 |
| *Bacillus polymyxa* | IAM | 1189 | (3) | 30° C | " | 57.0 | 0.77 |
| *Bacillus subtilis* | IFO | 3023 | (3) | 30° C | " | > 100 | 0.61 |
| *Micrococcus lysodeikticus* | IFO | 3333 | (1) | 27° C | " | 34.0 | 0.54 |
| *Aeromonas hydrophila var formicans* | ATCC | 13136 | (2) | 27° C | " | 6.0 | 0.85 |
| *Cytophaga johnsonae* | ATCC | 17061 | (1) | 27° C | " | 6.3 | 0.90 |
| *Azotobacter agilis* | IFO | 3741 | (1) | 27° C | " | 2.1 | 0.19 |
| *Streptomyces flavochromogenes* | FERM- | P934 | (1) | 27° C | " | 5.5 | 0.26 |
| *Candida tropicalis* | IFO | 0589 | (1) | 27° C | " | 0.9 | 0.13 |
| *Saccharomyces cerevisiae* | IFO | 0214 | (1) | 27° C | " | 1.1 | 0.18 |

Note:
In the table, "> 100" indicates that values over 100 were immeasurable due to excessively low maltase activity.

The enzymatic solution which gave the specified activity ratio of 21.3 showed no beta-amylase activity. The enzymatic solution aliquot obtained by the above mentioned 5-hour treatment was concentrated after dialysis, and then was applied to DEAE-Sephadex A-50 column (a product of Pharmacia AB, Uppsala, Sweden) equilibrated with a 0.02M phosphate buffer, pH 7.0, and was eluted using a 0-0.5M sodium chloride as solvent. As a result, the maltotriase portion was separated into, respectively, alpha-amylase portion and maltase portion.

The thus obtained maltotriase showed an activity which was 5.8 fold higher than that on starch, but hardly any dextrinogenic activity and its specified activity ratio was higher than 100.

Culture broths of *Bacillus cereus* IFO 3001, *Bacillus firmus* IFO 3330, *Bacillus polymyxa* IAM 1189 and *Bacillus subtilis* IFO 3023 were treated similarly to that of *Bacillus megaterium* FERM-P937, and enzymes with the specified activity ratio higher than 100 were obtained. The properties of the enzymes were similar to those of the *Bacillus megaterium* enzyme.

In the enzymatic solution obtained from the culture broth of *Flavobacterium suaveolens* IFO 3752, it was possible to increase the specified activity ratio to 12.4 by allowing the solution to stand at pH 8.5 and 35° C for 5 hours.

EXPERIMENT 5

The various enzymatic solutions obtained from *Bacillus megaterium* FERM-P937 according to the procedure described in Experiment 4 were used to determine the effects of the specified activity ratio on maltose contents in the resulting saccharified starch products. The solutions were each added to a commercialized starch hydrolysate in which maltose is the predominant composition in an amount of one unit of maltotriase per gram starch hydrolysate, d.s.b., and the mixtures were subjected to saccharification at pH 6.0 and 45° C for 22 hours. The results were as shown in Table V.

Table V

| Specified activity ratio | Sugar composition, % | | | |
|---|---|---|---|---|
| | $G_1$ | $G_2$ | $G_3$ | Dext |
| Non added | 0.6 | 91.5 | 5.2 | 2.7 |
| 1.3 | 6.8 | 90.7 | 0.7 | 1.8 |
| 2.7 | 4.6 | 93.1 | 0.6 | 1.7 |
| 9.6 | 3.3 | 94.2 | 0.6 | 1.9 |
| 21.3 | 2.8 | 94.8 | 0.6 | 1.8 |

As apparent from Table V, the specified activity ratio of higher than 2.5 decomposed maltotriose well and its use increased substantially the maltose purity of the saccharified starch product.

The invention will now be further described with reference to the following Examples.

Example I

One part of potato starch and ten parts of water containing five units of bacterial liquefying alpha-amylase per gram starch were prepared into a suspension with stirring. After bringing the pH to 6.0, the suspension was heated to 80°–90° C to effect simultaneous gelatinization and liquefaction, and then heated immediately up to 130° C where it was kept for 5 minutes. The reaction was effected as to attain a D.E. of not higher than 1.0. Following a quick cooling of the resultant to 50° C, a starch-debranching enzyme prepared from a culture broth of *Escherichia intermedia* ATCC 21073 and a soybean beta-amylase (product No. 1500 of Nagase & Co., Ltd., Osaka, Japan) were added to the resultant in respective amounts of 20 units per gram starch, and the mixture was subjected to saccharification at pH 6.0 for 46 hours (hydrolysate "A"). The sample withdrawn at 24 hours after starting the saccharification and that obtained after enzymatic inactivation of the 46 hours saccharification hydrolysate, were designated respectively hydrolysates "B" and "C". Hydrolysates "B" and "C" were then subjected to additional saccharification for 22 hours after which there was added to each the supernatant of wheat-germ extract obtained in Experiment 1 (specified activity ratio of 3.10) in respective amounts of one unit per gram starch and the resulting products were designated products "b" and "c". The results are given in Table VI.

Table VI

|   | Sugar composition, % | | | |
|---|---|---|---|---|
|   | $G_1$ | $G_2$ | $G_3$ | Dext |
| A | 0.6 | 91.5 | 5.2 | 2.7 |
| b | 2.5 | 96.1 | 0.4 | 1.0 |
| c | 2.5 | 95.2 | 0.8 | 1.5 |

After heating to inactivate enzymatic activities, the saccharified starch products were filtered, decolorized with activated carbon, deionized with ion exchange resins (H and OH types), and concentrated in vacuo. The yield for the concentrates was about 97% based on material starch, d.s.b. The product obtained by crystallization was investigated as to crystalline shape, size and appearance, as compared to the centrifugation period, and calculated on yield of crystalline maltose (total yield of first and second crystals) based on the saccharified starch products, d.s.b. The results obtained from saccharified starch hydrolysate "A," and from starch-products "b" and "c", which were designated, respectively, as "A'", "b'" and "c'", are listed in Table VII.

Table VII

|   | Crystalline shape, size and appearance | Centrifugation period ratio | Yield of crystalline maltose, % |
|---|---|---|---|
| A' | Good | 100 | 35.0 |
| b' | Excellent | 38 | 72.6 |
| c' | " | 43 | 65.3 |

It is apparent from the above results that a considerable improvement in maltose purity in saccharifed starch product is attainable whether maltotriase is added to the starch hydrolysates during the saccharification process with a combination of beta-amylase and starch-debranching enzyme or after saccharification with such combination. In addition, as shown in Table VII, with the employment of the maltotriase the centrifugation period can be reduced to about ½-⅓ to that required without the e employment, as well as the attainment of maltose purity improvement, and the yield of crystalline maltose approximately doubles. In view of reduction in the saccharification period, it is preferable to add the maltotriase of the present invention during the saccharification process so that is would act along with other enzymes.

EXAMPLE II

A suspension consisting of one parts sweet potato and three part water containing five units of alpha-amylase per gram starch was adjusted with stirring to pH 5.5. Thereafter the suspension was maintained in a temperature range of 80°–90° C to effect simultaneous gelatinization and liquefaction and when a D.E. of 19 was attained the resultant was heated immediately to 120° C where it was maintained for five minutes, whereupon it was cooled rapidly to 50° C. Then the same beta-amylase used in Example I and a starch-debranching enzyme prepared from a culture broth of Pseudomonas amyloderamosa ATCC 21262 were added to the resultant in respective amounts of ten units per gram starch. The mixture was subjected to saccharification for 24 hours while maintaining the pH at 5.5 and temperature at 50° C. Separately, to another portion of the same mixture was added the supernatant of canary seed obtained in Experiment 1 and with the specified activity ratio of 6.24 in an amount of 0.2 units of maltotriase activity per gram starch, and allowed saccharification for 24 hours. The results were as listed in Table VIII.

Table VIII

| Maltotriase | Sugar composition, % | | | |
|---|---|---|---|---|
|   | $G_1$ | $G_2$ | $G_3$ | Dext |
| Non-added | 8.1 | 65.3 | 18.6 | 8.0 |
| Added | 14.0 | 77.1 | 2.7 | 6.2 |

After purification and concentration of the resulting saccharified starch products according to the methods described in Example I, the product saccharified without an addition of maltotriase was found noncrystallizable while the starch product saccharified with the maltotriase was crystallizable. The yields of the products in powder form which were obtained by spray-dying said concentrated products were both about 96% based on material starch, d.s.b. The powder product prepared from the maltotriase-saccharified starch product possessed a characteristic gloss and a much more improved commercial value.

EXAMPLE III

A suspension of one part corn starch and two parts water was adjusted to a pH of about 2.5, charged into a converter where the suspension was autoclaved at a pressure of 1.8-2.0kg/cm$^2$ with steam for about ten minutes to attain D.E. 20. After adjusting the pH to 6.0 the resultant was maintained at 50° C, beta-amylase derived from wheat bran was added in an amount of two units per gram starch, and then subjected to saccharification for 24 hours. To aliquots of a saccharified starch hydrolysate obtained after 12 hours under the same conditions was added one member of a group consisting of supernatants of a rice-bran extract which possessed the specified activity ratio of 11.6, a barley malt extract (specified activity ratio=9.94) and potato extract (specified activity ratio=8.17) obtained in Experiment 1, in an amount of 0.5 units of maltotriase activity per gram starch and the mixture was then subjected to an additional 12 hours of saccharification. The results were as listed in Table IX.

Table IX

| Maltotriase source | Sugar composition, % | | | |
|---|---|---|---|---|
|   | $G_1$ | $G_2$ | $G_3$ | Dext |
| Non-added | 4.7 | 52.8 | 22.5 | 20.0 |
| Rice bran | 11.4 | 67.1 | 3.8 | 17.7 |
| Barley germ | 11.0 | 68.3 | 4.2 | 16.5 |
| Potato | 12.3 | 65.5 | 4.0 | 18.2 |

The saccharified starch products were purified similarly as in Example I and syrup products were obtained in respective yields of about 98% based on starch, d.s.b. The employment of the enzyme of the present invention not only substantially increased the maltose content in the resulting saccharified starch products in comparison with conventional starch syrups, but, additionally, increased fermentable sugars about 1.5 fold. Thus the saccharified starch products of the invention are suitable in the preparations of food products involving fermentation, such as bakery products.

EXAMPLE IV

To starch hydrolysates prepared similarly as the hydrolysates "B" and "C" of Example I was added an enzyme solution (the specified activity ratio higher than 100) obtained from *Xanthomonas citri* IFO 12213 in an amount of one unit of maltotriase activity per gram starch, and the resulting mixtures were saccharified at 45° C, pH 6.0 for 22 hours. The results of the resulting saccharified starch products, designated as "B'" and "C'", are listed in Table X.

Table X

| | Sugar composition, % | | | |
|---|---|---|---|---|
| | G₁ | G₂ | G₃ | Dext |
| A | 0.6 | 91.5 | 5.2 | 2.7 |
| B' | 2.6 | 96.1 | 0.3 | 1.0 |
| C' | 2.5 | 95.0 | 0.6 | 1.9 |

The saccharified starch products were purified and concentrated similarly as in Example I. The yields of the concentrated products were respectively about 97% based on material, d.s.b. The products were prepared into crystalline form and compared on crystalline shape, size and appearance, centrifugation period and yield of crystalline maltose (total of first and second crystals) based on saccharified starch products, d.s.b. The results obtained from saccharified starch hydrolysate "A", and from starch products "B'" and "C'", which were designated, respectively, as "A'", "B''", "C''", are listed in Table XI.

Table XI

| | Crystalline shape, size and appearance | Centrifugation period ratio | Yield of crystalline maltose, % |
|---|---|---|---|
| A' | Good | 100 | 35.0 |
| B'' | Excellent | 36 | 72.3 |
| C'' | " | 45 | 64.5 |

As the above table shows, the remarkable effect of the maltotriase is evident whether the maltotriase is added to the material starch hydrolysate during the saccharification process with the combination of beta-amylase and starch-debranching enzyme or after saccharification with the such enzyme combination. Moreover, as shown in the same table, with the employment of the maltotriase, a reduction of the centrifugation period to about ½–⅓ and an elevation of the crystalline maltose yield of about double fold were realized. In view of reduction of the saccharification period, it is preferable that the maltotriase is added at a stage so that it would act effectively along with other enzymes. The purified crystalline maltose is especially suited for intravenous use.

EXAMPLE V

To the saccharified starch hydrolysate "C" obtained in accordance with the procedure described in Example IV one member each of the enzyme solutions derived from various bacteria obtained in Experiment 3 was added in respective amount of one unit of maltotriase activity per gram material starch hydrolysate and then the mixtures were subjected to saccharification for 22 hours. The only exception was that purified enzyme preparations obtained in accordance with the procedure described in Experiment 4 were used in the cases of *Bacillus subtilis* IFO 3023 and *Bacillus polymyxa* IAM 1189. The sugar compositions for the resulting starch products are listed in the following table.

Table XII

| Maltotriase source | | Sugar composition, % | | | |
|---|---|---|---|---|---|
| | | G₁ | G₂ | G₃ | Dext |
| Non-added | | 0.6 | 91.5 | 5.2 | 2.7 |
| *Pseudomonas amyloderamosa* | ATCC 21262 | 3.5 | 94.8 | 0.5 | 1.2 |
| *Escherichia coli* | IFO 3044 | 3.6 | 94.0 | 0.8 | 1.6 |
| *Enterobacter aerogenes* | ATCC 9621 | 4.0 | 93.7 | 0.6 | 1.7 |
| *Erwinia aroideae* | IFO 3830 | 3.6 | 95.1 | 0.4 | 0.9 |
| *Sarcina variabilis* | IFO 3067 | 3.4 | 94.3 | 0.8 | 1.5 |
| *Bacillus polymyxa* | IAM 1189 | 3.5 | 94.7 | 0.5 | 1.3 |
| *Bacillus subtilis* | IFO 3023 | 3.5 | 94.6 | 0.5 | 1.4 |
| *Micrococcus lysodeikticus* | IFO 3333 | 3.4 | 94.2 | 0.7 | 1.7 |
| *Aeromonas hydrophila var formicans* | ATCC 13136 | 3.6 | 95.1 | 0.3 | 1.0 |
| *Cytophaga johnsonae* | ATCC 17061 | 4.4 | 93.4 | 0.6 | 1.6 |

The saccharified products were then purified and concentrated in accordance with the procedures and under the conditions as described in Example I. The yields of the concentrated products were each about 97% based on material, d.s.b. The concentrated products were then crystallized and the crystalline products were compared as to crystalline shape, size and appearance, centrifugation period, and yield of crystalline maltose (total of first and second crystals) based on material saccharified starch solution, d.s.b. The results were as listed in Table XIII.

As apparent from Table XIII, the employment of the maltotriase of the invention resulted in the improvement of maltose purity as well as in the reduction of the centrifugation period to about ½–⅓ and the approximate doubling of the crystalline maltose yield.

EXAMPLE VI

After pH adjustment to about 2.5, a starch suspension consisting of one part corn starch and two parts water was charged into a converter where the suspension was liquefied to D.E. 20 by subjection to steam at 1.8–2.0kg/cm² for ten minutes, adjusted to pH 6.0 and cooled to 50° C. While maintaining the temperature, to the liquefied starch solution was added two units of wheat-bran beta-amylase preparation per gram material starch and reacted for 24 hours.

Each of the various bacterial enzymes obtained in Experiment 3 was added to portions of starch hydrolysates obtained by 12 hours of saccharification under the same conditions in respective amounts of 0.5 units of maltotriase per gram starch and the mixtures were Table XIII

| Maltotriase source | | Crystalline shape, size and appearance | Centrifugation period ratio | Yield of crystalline maltose, % |
|---|---|---|---|---|
| Non-added | | Good | 100 | 35.0 |
| Pseudomonas amyloderamosa | ATCC 21262 | Excellent | 40 | 67.2 |
| Escherichia coli | IFO 3044 | " | 42 | 66.4 |
| Enterobacter aerogenes | ATCC 9621 | " | 50 | 60.1 |
| Erwinia aroideae | IFO 3830 | " | 38 | 71.2 |
| Sarcina variabilis | IFO 3067 | " | 43 | 66.3 |
| Bacillus polymyxa | IAM 1189 | " | 41 | 67.1 |
| Bacillus subtilis | IFO 3023 | " | 41 | 66.9 |
| Micrococcus lysodeikticus | IFO 3333 | " | 43 | 65.3 |
| Aeromonas hydrophila var formicans | ATCC 13136 | " | 37 | 72.1 |
| Cytophaga johnsonae | ATCC 17061 | " | 56 | 58.0 | then subjected to saccharification for an additional 12 hours. The only exception was that in cases of *Bacillus cereus* IFO 3001, *Bacillus firmus* IFO 3330 and *Bacillus metaterium* FERM-P937 purified preparations obtained in Experiment 4 were used.

The results were as listed in Table XIV.

The saccharifed starch products were then purified, concentrated similarly as in Example I and syrup products were obtained in respective yields of about 98% based on material starch, d.s.b. The employment of the maltotriase not only increased significantly the maltose purity of the saccharified starch products, but in addition increased fermentable sugars about 1.4 fold. The saccharified starch products prepared in accordance with the present invention are suitable in processing food products, involving fermentation, for example bakery products.

Table XIV

| Maltotriase source | | Sugar composition, % | | | |
|---|---|---|---|---|---|
| | | $G_1$ | $G_2$ | $G_3$ | Dext |
| Non-added | | 4.7 | 52.8 | 22.5 | 20.0 |
| Pseudomonas iodinum | IFO 3558 | 13.0 | 63.5 | 5.2 | 18.3 |
| Xantomonas citri | IFO 12213 | 11.2 | 68.1 | 4.1 | 16.6 |
| Flavobacterium suaveolens | IFO 3752 | 15.3 | 61.4 | 6.2 | 17.1 |
| Escherichia coli | IFO 3044 | 12.5 | 65.3 | 4.5 | 17.7 |
| Klebsiella neumoniae | ATCC 8724 | 13.0 | 62.8 | 6.2 | 18.0 |
| Lactobacillus plantarum | ATCC 8008 | 12.6 | 65.2 | 5.3 | 16.9 |
| Arthrobacter simplex | IAM 1660 | 13.2 | 63.7 | 5.9 | 17.2 |
| Bacillus cereus | IFO 3001 | 12.9 | 63.8 | 5.2 | 18.1 |
| Bacillus firmus | IFO 3330 | 12.4 | 64.7 | 5.0 | 17.9 |
| Bacillus megaterium | FERM-P937 | 13.1 | 64.8 | 4.8 | 17.3 |
| Aeromonas hydrophila var formicans | ATCC 13136 | 11.8 | 68.2 | 3.9 | 16.1 |
| Cytophaga johnsonae | ATCC 17061 | 11.4 | 66.8 | 4.3 | 17.5 |
| Streptomyces flavochromogenes | FERM-P934 | 12.6 | 65.7 | 4.2 | 17.5 |

What is claimed is:

1. A process for improving maltose purity of saccharified starch products, comprising:

subjecting a starch hydrolysate with a 50% or more maltose purity to the action of an enzyme with a maltotriase decomposing activity versus maltose-decomposing activity ratio of 100 or higher, an optimal pH range from about 5.0 to 7.0, and optimal temperature range from about 45° to 55° C, a stable pH range of about 4.5 to 10.0, a stable temperature range not higher than 55° C, maltotriose decomposing activity several times higher than starch decomposing activity and substantially no dextrinogenic activity.

2. In a process for saccharifying starch products in which starch products are hydrolyzed to a maltose content of 50% or more, the improvement whereby maltose purity is increased, comprising:

subjecting said starch hydrolyzate to the action of an enzyme with a maltotriose-decomposing activity versus maltose-decomposing activity ratio of 100 or higher, an optimal pH range from about 5.0 to 7.0, and optimal temperature range from about 45° to 55° C, a stable pH range of about 4.5 to 10.0, a stable temperature range nto higher than 55° C, maltotriose decomposing activity several times higher than starch decomposing activity and substantially no dextrinogenic activity.

3. A process in accordance with claim 2, wherein said subjecting step takes place during said hydrolysis of the starch products.

4. A process in accordance with claim 2, in which said subjecting step takes place after said hydrolysis of the starch product to a maltose content of 50% or more.

* * * * *